(12) United States Patent
Bjarnsholt et al.

(10) Patent No.: US 11,376,230 B2
(45) Date of Patent: Jul. 5, 2022

(54) WOUND CARE PRODUCT

(75) Inventors: Thomas Bjarnsholt, Soborg (DK);
Klaus Kirketerp-Moller, Koge (DK);
Michael Christian Givskov,
Humlebaek (DK)

(73) Assignees: Rigshospitalet Copenhagen University Hospital, Copenhagen (DK);
Bispebjerg Hospital, Copenhagen (DK)

( * ) Notice: Subject to any disclaimer, the term of this patent is extended or adjusted under 35 U.S.C. 154(b) by 92 days.

(21) Appl. No.: 14/112,518

(22) PCT Filed: Apr. 18, 2012

(86) PCT No.: PCT/DK2012/050130
§ 371 (c)(1),
(2), (4) Date: Oct. 17, 2013

(87) PCT Pub. No.: WO2012/143013
PCT Pub. Date: Oct. 26, 2012

(65) Prior Publication Data
US 2014/0046276 A1    Feb. 13, 2014

(30) Foreign Application Priority Data
Apr. 18, 2011 (EP) .................... 1162912

(51) Int. Cl.
| A61K 31/194 | (2006.01) |
| A61L 26/00 | (2006.01) |
| A61L 15/46 | (2006.01) |
| A61F 13/02 | (2006.01) |
| A61K 9/70 | (2006.01) |
| A61M 1/00 | (2006.01) |
| A61K 9/00 | (2006.01) |

(52) U.S. Cl.
CPC ........ *A61K 31/194* (2013.01); *A61F 13/0206* (2013.01); *A61F 13/0216* (2013.01); *A61K 9/7007* (2013.01); *A61L 15/46* (2013.01); *A61L 26/0066* (2013.01); *A61M 1/0023* (2013.01); *A61K 9/0014* (2013.01); *A61L 2300/102* (2013.01); *A61L 2300/404* (2013.01); *Y02A 50/30* (2018.01)

(58) Field of Classification Search
CPC .......... A61K 31/194; A61K 9/70–7092; A61K 9/7007; A61M 1/00; A61F 13/00063; A61L 2300/404; A61L 2300/406; A61L 2300/00; A61L 2300/20; A61L 15/20
See application file for complete search history.

(56) References Cited

U.S. PATENT DOCUMENTS

| 4,366,170 A | 12/1982 | Engelhart et al. |
| 5,340,836 A | 8/1994 | Reinhard et al. |
| 5,470,585 A * | 11/1995 | Gilchrist ............. A01N 25/08 424/409 |
| 5,480,658 A | 1/1996 | Melman |
| 6,001,345 A | 12/1999 | Askill et al. |
| 6,019,905 A | 2/2000 | Waggoner |
| 6,106,854 A | 8/2000 | Belfer et al. |
| 6,436,445 B1 | 8/2002 | Hei et al. |
| 6,635,035 B1 | 10/2003 | Marasco et al. |
| 6,762,160 B2 | 7/2004 | Barbeau et al. |
| 6,812,196 B2 | 11/2004 | Rees et al. |
| 2001/0046979 A1 | 11/2001 | Roselle et al. |
| 2002/0177624 A1 | 11/2002 | Hanna et al. |
| 2005/0175748 A1* | 8/2005 | Thijssen ............. A01N 25/10 426/326 |
| 2005/0250821 A1 | 11/2005 | Sewalt et al. |
| 2005/0287181 A1 | 12/2005 | Murthy |
| 2006/0025727 A1 | 2/2006 | Boehringer |
| 2006/0159730 A1* | 7/2006 | Simon ............. A61Q 5/12 424/443 |
| 2007/0010798 A1 | 1/2007 | Stoller |
| 2007/0011625 A1 | 7/2007 | Brown |
| 2007/0202138 A1 | 8/2007 | Funt |
| 2007/0244449 A1 | 10/2007 | Najafi et al. |
| 2007/0292397 A1 | 12/2007 | McNulty et al. |
| 2008/0125742 A1 | 5/2008 | Podhajsky |
| 2008/0318834 A1* | 12/2008 | Cadee ............. A01N 37/46 514/1.1 |
| 2009/0054855 A1 | 2/2009 | Blott |
| 2009/0163449 A1* | 6/2009 | Wempe ............. A61K 9/19 514/159 |

(Continued)

FOREIGN PATENT DOCUMENTS

| CN | 101293109 A * | 10/2008 |
| DE | 198 01 209 | 7/1999 |

(Continued)

OTHER PUBLICATIONS

Martineau et al.: "Biofilm reduction by a new burn gel that targets nociception", J Appl Microb, vol. 103, pp. 297-304, 2007.
Hisanori et al.: "Effects of acetic acid on biofilms formed by *Staphylococcus aureus*", Archives of Dermatological Research, Springer, International, Berlin, DE, vol. 291, No. 10, Oct. 1, 1999, pp. 570-573.
510K Summary; GelSpray Liquid Bandage 510k Summary; Submitter: BioCure, Inc. (5 Pages).
Akiyama, Hisanori et al., "Effects of acetic acid on biofilms formed by *Staphylococcus aureus*" Arch Dermatol Res, 1999, pp. 570-573, vol. 291.

(Continued)

*Primary Examiner* — Tatyana Zalukaeva
*Assistant Examiner* — Meagan Ngo
(74) *Attorney, Agent, or Firm* — Brown Rudnick LLP; Thomas C. Meyers (57) ABSTRACT

The present invention pertains to use of sodium diacetate ($NaHAc_2$) as an antimicrobial agent against bacteria growing in biofilms. The aspects of the invention include a wound care product comprising sodium diacetate, a kit comprising a wound care product, and a method of treating an infected wound.

8 Claims, 4 Drawing Sheets

(56) References Cited

U.S. PATENT DOCUMENTS

| | | |
|---|---|---|
| 2010/0030132 A1 | 2/2010 | Niezgoda |
| 2010/0051035 A1 | 3/2010 | Jenkins et al. |
| 2010/0068279 A1 * | 3/2010 | Hartwell ............... A61K 31/198 424/486 |
| 2011/0171283 A1 | 7/2011 | Riesinger |
| 2013/0196951 A1 | 8/2013 | Schoenfisch et al. |

FOREIGN PATENT DOCUMENTS

| | | |
|---|---|---|
| EP | 0 763 359 A1 | 3/1997 |
| EP | 1 068 873 | 1/2001 |
| WO | WO 2005/058381 A1 | 6/2005 |
| WO | 2005123057 A1 | 12/2005 |
| WO | WO 2008/013896 A2 | 1/2008 |
| WO | WO 2008/040020 A2 | 4/2008 |
| WO | WO 2008/129318 A2 | 4/2008 |
| WO | 2008064475 A1 | 6/2008 |
| WO | 2009155931 A1 | 12/2009 |
| WO | WO 2010148357 A1 * | 12/2010 ............ C02F 1/5263 |
| WO | 2011076216 A2 | 6/2011 |

OTHER PUBLICATIONS

Christensen, B. B. et al., "Molecular tools for study of biofilm physiology" Methods Enzymol, 1999, pp. 20-42, vol. 310.

Doyle, Ronald, "Microbial Growth in Biofilms: Special environments and physicochemical aspects," 2001, pp. 114-115, Gulf Professional Publishing.

Hu, Li Donghong, "Biologic external application medicine for curing wound" PN—CN1724079/PD—Jan. 25, 2006; XP-002583716.

Milner. "Acetic acid to treat Pseudomonas aeruginosa in spuperficial wounds and burns." The Lancet. Jul. 4, 1992. 340, 8810:61.

Novick, Richard, "Properties of a Cryptic High-Frequency Transducing Phage in *Staphylococcus aureus*" Virology, 1967, pp. 155-166, vol. 33.

O'Toole, G. A. et al., "Genetic approaches to study of biofilms" Methods Enzymol, 1999, pp. 91-109, vol. 310.

\* cited by examiner

WOUND CARE PRODUCT

CROSS-REFERENCE TO RELATED APPLICATIONS

This application is the national phase under 35 U.S.C. § 371 of PCT International Application No. PCT/DK2012/050130, filed Apr. 18, 2012, which claims the benefit of EP Patent Application No. 11162912.7, filed Apr. 18, 2011, the entire contents of the aforementioned applications are hereby incorporated herein by reference.

TECHNICAL FIELD OF THE INVENTION

The present invention relates to a wound care product comprising sodium diacetate (NaHAc$_2$) as an antimicrobial agent for the treatment of microbial infections comprising biofilms. The aspects of the invention include a wound care product, a kit comprising a wound care product, and a method of treating an infected wound.

BACKGROUND OF THE INVENTION

Microbes, in particular bacteria, are known to cause various types of infections in both humans and animals. Antibiotics can be used to either kill or inhibit the growth of unwanted microbes and it is usually the choice of treatment for infections. However, the world wide increase in antibiotic resistant microbes has limited the effect of traditional treatments making it very difficult to treat infections that were once treatable. A particular problem is infections were the bacteria are capable of forming a so called bacterial biofilm as such infections typically tolerate the highest deliverable doses of antibiotics. Such infections develop commonly in wounds, which as a result, can develop into chronic wounds. Due to this antibiotic resistance and tolerance it is important to devise new treatment scenarios which efficiently enable eradication of unwanted microbes. Furthermore, in relation to infections in humans or animals it is imperative that the treatment is non-toxic to the hosts and physiologically acceptable. It has been disclosed that aqueous compositions comprising acetic acid are capable of inhibiting the growth and even eradicating certain bacteria having formed microbial biofilm. For example WO 2009/155931 describes buffered acetic acid compositions and there use in the treatment of bacterial biofilm infections, while Martineau L and Dosch H M (2007), Journal of Applied Microbiology, 103, 297-304 describes biofilm reduction by a burn gel comprising acetic acids and citric acid.

Acetic acid is a liquid at ambient pressure and temperature, and therefore any compositions comprising acetic acid are liquid or wet compositions. Therefore wound care products comprising acetic acid are by definition wet and this has implications in relation to handling, packaging, and odour. Acetic acid also has reduced efficacy against biofilm outside a relatively narrow pH interval, and must be used in relatively high concentrations.

In relation to wound care a number of products have been developed which have the combined effect of protecting the wound from the surrounding environment and enabling the delivery of compositions comprising active substances to the wound area. WO2005/123057 describes a wound care product for reducing and/or preventing bacterial infections of wounds comprising a composition including at least two weak organic acids and EDTA, along with bandage material. US 2010/0068279 discloses a polymeric dressing for the treatment of skin injuries, particularly burns. In paragraph [0022] it is stated that the dressing may contain means of preventing infections, such as antimicrobials including sodium diacetate among others. A dressing comprising sodium diacetate is not explicitly exemplified, and neither is any effect on biofilm bacteria.

Hence, improved or alternative wound care products comprising an effective antibacterial composition would be advantageous, and in particular wound care products comprising a composition of an a antimicrobial compounds with high efficacy at low concentrations and within a broader range of pH values would be advantageous.

SUMMARY OF THE INVENTION

Thus, an object of the present invention relates to the provision of improved or alternative wound care products. In particular, it is an object of the present invention to provide an improved wound care product comprising an safe and effective antibacterial component which has the ability to kill or inhibit the growth otherwise resistant biofilm forming bacteria that solves the above mentioned problems of the prior art with compositions of weak organic acids which are administered in high concentrations and are effective only within a narrow pH interval.

The inventors have surprisingly found that wound care products comprising sodium diacetate (NaHAc$_2$) are effective at killing biofilm forming microbes in a broader pH interval and at low concentrations.

Thus, one aspect of the invention relates to a wound care product comprising sodium diacetate.

Another aspect of the present invention relates to a wound care product comprising sodium diacetate for use in treatment of a wound.

A third aspect of the present invention is a method of treating a wound comprising the step of
 a) applying a wound care product comprising sodium diacetate to a wound.

Yet another aspect of the present invention is to provide a kit comprising a wound care product comprising sodium diacetate and an adhesive membrane.

The present invention will now be described in more detail in the following.

DETAILED DESCRIPTION OF THE INVENTION

Wound Care Product Comprising Sodium Diacetate

The first aspect of the present invention is a wound care product comprising sodium diacetate.

By "wound care product" is meant any product applicable to a wound which may comprise the active ingredients of the invention. Such products are typically referred to as "dressings", which may be produced from a number of typically porous and/or absorbent materials as described below. The term "wound" is to be understood in its broadest sense, i.e. as any exterior part of a human or animal body that may be in need of treatment, particularly antibacterial treatment. Examples of wounds in the present context includes but are not limited to: Any laceration to the skin, such as a wound, a chronic wound, a burn wound, a cut, wounds associated with dermatological conditions, grafts, pressure wounds, traumatic wounds, underlying infections with fistulation from bone, joint or soft tissue, any insertion or extrusion point for medical equipment, such as a catheter, or a medical bone screw, pins, wires, rods artificial joints, plates, autografts, allografts or zenografts.

By "sodium diacetate" is meant the salt having the formula $NaHAc_2$ where "Ac" denotes an acetyl group. It may alternatively be denoted $NaH(C_2H_3O_2)_2$. Synonyms also covering sodium diacetate include: sodium hydrogen acetate, sodium hydrogen diacetate, E262, and $NaC_4H_7O_4$. Sodium diacetate crystals have acetic acid ($CH_3COOH$) firmly held into the crystal lattice of neutral sodium acetate ($CH_3COONa$), thereby preventing any odour of acetic acid. Sodium diacetate is recognized as safe ingredient (GRAS) by the US FDA, and is a generally permitted food additive in Europe (E 262) and elsewhere.

If sodium diacetate is provided for example in an aqueous solution the concentration of sodium diacetate may be 0.10-10% (W/V), 0.25-5%, 0.50-5%, 0.75-5%, 1.00-5%, 1.25-5%, 1.50-5% (W/V). Alternative said concentration may be 0.25-4% (W/V), 0.25-3%, 0.25-2% (W/V). Preferably, the concentration is 1.0-3.0% (W/V), 1.5-2%, 1.60-1.80% (W/V).

Specifically, in one embodiment a wound care product is provided wherein the comprised sodium diacetate is in dry form.

By "dry form" is meant a form of the sodium diacetate salt where it is essentially dry, i.e. it is not dissolved in a liquid composition, such as in an aqueous composition. Dry form does however not mean that the sodium diacetate is completely dry, i.e. entirely free of liquids. Sodium diacetate may absorb small amounts of water from the surrounding environment, and small amounts of liquids such as water may be added to avoid dust formation upon handling. Also, additional components added to the wound care device may be in liquid form. Thus, the sodium diacetate may contain up to 10% (W/W) water, such as 8%, 6%, 5%, 4%, 3%, 2%, 1%, 0.596, 0.1% ON/W) water. A dry form of sodium diacetate may be a powder, such as a micronized powder, and the dry form or powder may have a defined particle size. The particle size in terms of the particle diameter may preferably be lower than 4 mm, such as lower than 2 mm, 1 mm, 0.5 mm, 0.2 mm, 0.1 mm, 0.08 mm, 0.06 mm, 0.04 mm, 0.02 mm, 0.01 mm, 0.005 mm, 0.002 mm, such as lower than 0.001 mm. Alternatively the particle size may be in the range of 2-0.0001 mm, 1-0.0001 mm, 0.8-0.0001 mm, 0.5-0.0001 mm, 0.2-0.0001 mm, 0.1-0.0001 mm, or 0.01-0.0001 mm. When referring to ranges of particle sizes the particle size may be an average particle size.

The wound care product may in one embodiment be characterized by, that the sodium diacetate is comprised in a carrier device. The carrier device may be selected from the group consisting of a foam, gauze, dressing, gel, bandage or paste. The amount or concentration of sodium diacetate in the carrier device may vary according to material and also according to whether the sodium diacetate is distributed through the entire carrier device or only in a defined volume close to the surface of the carrier device, or a defined volume in the centre of the carrier device. Thus, in one embodiment an effective amount of sodium diacetate is embedded in the carrier device. An effective amount of sodium diacetate may be in the range of 0.01-200 $mg/cm^3$, 0.01-100 $mg/cm^3$, 0.01-75 $mg/cm^3$, 0.01-50 $mg/cm^3$, 0.01-40 $mg/cm^3$, 0.01-30 $mg/cm^3$, 0.01-20 $mg/cm^3$, 0.01-10 $mg/cm^3$, 0.01-5 $mg/cm^3$, 0.01-2 $mg/cm^3$, 0.01-1 $mg/cm^3$, 0.01-0.5 $mg/cm^3$, 0.01-0.4 $mg/cm^3$, 0.01-0.3 $mg/cm^3$, such as 0.05-5 $mg/cm^3$, 0.07-5 $mg/cm^3$, 0.1-5 $mg/cm^3$, 0.2-5 $mg/cm^3$, 0.3-5 $mg/cm^3$.

In an alternative embodiment an effective amount of sodium diacetate is distributed on a surface of the carrier device. This may be an exterior surface or an interior surface, such as a surface of a core material in the carrier device which is surrounded by another material. In this embodiment the effective amount of sodium diacetate may be in the range of 0.01-2 $mg/cm^2$, 0.01-1 $mg/cm^2$, 0.01-0.5 $mg/cm^2$, 0.01-0.4 $mg/cm^2$, 0.01-0.3 $mg/cm^2$, such as 0.05-2 $mg/cm^2$, 0.07-2 $mg/cm^2$, 0.1-2 $mg/cm^2$, 0.2-2 $mg/cm^2$, 0.3-2 $mg/cm^2$.

In another embodiment a wound care product is provided wherein the carrier device is a dressing. The dressing may comprise two or more layers. Said dressing may comprise one or two outer layers surrounding a core layer and wherein the core comprises an absorbent material. Alternatively the entire dressing consists of an adsorbent material.

The absorbent material of the dressing may preferably be selected from the group consisting of polyurethane-ether, polyacrylate, cellulose, polypropylene fibres, gauze, alginate, agar, or mixtures thereof. The outer layers of the dressing may comprise a material selected from non-woven polypropylene fibres, viscose or cotton (gauze). Alternatively the entire carrier device consists of said absorbent material. Dressings may also comprise micropore materials and/or one-way membranes such as Goretex®, Gortex® or similar materials. The sodium diacetate may be embedded in the dressing in dry or wet form and it may be embedded in the outer layer or in the absorbent core layer or on the surface of any of these layers.

Depending on the carrier device the wound care product comprising sodium diacetate may be furnished in various ways. If the carrier device is a solid material the sodium diacetate may be added directly to the device or it may be added in solution and the device may optionally be dried. If the carrier device is a gel or paste the sodium diacetate may be incorporated therein in solid form, such as a suspended powder.

In one embodiment the wound care product is characterised in that the sodium diacetate is the only active ingredient in the product. Particularly it may be the only antimicrobial and/or antibacterial ingredient in the product. Another embodiment of the invention is a wound care product essentially consisting of a carrier device and sodium diacetate.

The wound care product may alternatively comprise at least one additional antimicrobial substance. The antimicrobial substance may preferably be an antibiotic, selected from the group consisting of amino glycosides, macrolides, fluoroquinolones, ceftazidimes, tetracyclines, sulfonamides, beta-lactams, oxazolidiones, antimicrobial peptides. In particular the antibiotic compounds tobramycin, ciprofioxaxine, and colistin has been proven effective in the treatment of infected wounds comprising biofilm forming bacteria when combined with sodium diacetate.

Alternatively the antimicrobial substance is selected from the group consisting of xylitol, framycetin, fusidic acid, nitrofural, phenylmercuric nitrate, benzododecinium, triclosan, cetylpyridinium, aluminium chlorohydrate, povidone-iodine, clioquinol, benzalkonium, chlorhexidine, iodoform, hypochloric acid. In another embodiment the antimicrobial substance is silver (Ag). The silver may either be in its ionic form $Ag^+$, e.g. as a silver salt or as silver metal e.g. nanosized silver particles. In particular silver sulfadiazine may be comprised in the product.

The wound care product may in another embodiment further comprise at least one growth factor, such as transforming growth factor, epidermal growth factor, platelet derived growth factor, insulin-like growth factor, keratinocyte growth factor, fibroblast growth factor, granulocyte macrophage colony stimulating growth factor, granulocyte colony stimulating growth factor or local anesthetics.

The wound care product may also further comprise a compound selected from the group consisting of pH indicator, Ringer's solution and isotonic saline. In embodiments where sodium diacetate is used in dry form, the above compounds may be positioned in separate compartments of the wound care product.

Use of a Wound Care Product in the Treatment of Microbial Biofilm Infections

Another aspect of the present invention is the wound care product as described above for use in treatment of wound infections comprising microbial biofilm, in particular bacterial infections comprising biofilm forming bacteria.

By "microbial biofilm" is meant an aggregate of microbes growing within a film generated by said microbes. Microbes may grow as individual organisms planktonic or proliferate into aggregates also known as microbial biofilms. Biofilms are often found in chronic bacterial infections in or on humans and are known to be very difficult to eradicate with conventional antibiotics. Microbial biofilm infections may be discerned from acute bacterial infections by (i) the infection persist despite antibiotic therapy and the innate and adaptive immune and inflammatory responses of the host and (ii) in contrast to colonisation, are characterised by an immune response and persisting pathology. The diagnosis of microbial biofilm infections in wounds is described in Høiby N, et al., Antibiotic resistance of bacterial biofilms, Int J Antimicrob Agents. 2010, 35(4), page 323 (Table 1) and section 2. last paragraph (page 323 left column).

The biofilm forming bacteria causing the infections described above may be selected from the group consisting of Gram-negative bacteria, Gram-positive bacteria, proteobacteria, anaerobic or aerobic bacteria. Examples of such bacteria may be selected from the group consisting of, but are not limited to *P. aeruginosa, E. coli* including ESBL, *Klebsiella pneumoniae*, including ESBL and aureus, including MRSA.

The infected wound may preferably be a chronic wound. It may also be selected from the group consisting of a wound on or around an implant, a wound on or around a prosthetic device, a wound in or around catheters, or a wound in or around the oral cavity, where these wounds may or may not be chronic.

By "chronic wound" is meant a wound which does not heal if left untreated. Chronic wounds may often be infected by opportunistic bacteria, for example due to a patient having a reduced immune response. The opportunistic bacteria may often be biofilm forming bacteria.

The infected wound may be in a patient with reduced immune response. The reduced immune response may be caused by a condition selected from the group consisting of cystic fibrosis, diabetes, obesity, malnutrition, drug abuse, and treatment with medication that reduces the immune response.

The treatment of wound infections comprising microbial biofilm may be a negative pressure wound therapy treatment. In particular, the wound care product for use in treatment of bacterial infections in combination with Negative Pressure Wound Therapy has been shown to be effective, and the wound care product is adapted to such use, i.e. for example the dressing is made of a material well suited for use in Negative Pressure Wound therapy. The Negative Pressure Wound Therapy (NPWT) method is also known as Topical Negative Pressure (TNP) method, Sub-atmospheric Pressure Dressing (SPD) method, or Vacuum Sealing Technique (VST) method. These methods are known to the skilled person, and have among others the advantages of removing wound fluids and desiccated tissue, improving blood flow in the wound, and decreasing levels of bacteria in the wound. In the present context it may also help to remove excess or "spent" volumes of the active composition and/or the wound fluids comprising dissolved sodium diacetate while aiding the flow or dispersion of sodium diacetate from the carrier material into the wound area.

Another aspect of the present invention is a method of treating a wound comprising the step of:
a) applying a wound care product as described above to a wound.

Preferably the wound is an infected wound. The infected wound may be infected with bacteria. The bacteria may be selected from the group consisting of gram-negative bacteria, gram-positive bacteria, proteobacteria, anaerobic or aerobic bacteria. Particularly the bacteria may be selected from, but not limited to *P. aeruginosa, E. coli*, including ESBL, *Klebsiella pneumoniae*, including ESBL, and *S. aureus*, including MRSA. In a preferred embodiment the bacterial infections are infections comprising microbial biofilm.

This method may be repeated, i.e. removal of the initial wound care product and application of a fresh wound care product with regular intervals may be performed until the infection is eradicated. The wound care product may be applied for a period the range of 0.5-18 h, such as 1-12 h, such as 2-8 h, such as 3-6 h, such as 4 h. It may alternatively be applied for shorter periods such as 10-40 min, such as 15-35 min, preferably 20-30 min, in between replacements.

The method may further comprise the steps of:
b) applying negative pressure to the wound for 0.5-18 hours,
c) adjusting the pressure to ambient pressure
d) removing the wound care product from the wound,
e) optionally repeating steps a)-d)

The negative pressure may be in the range of −200 to −50 mmHg, such as −150 to 60 mmHg, preferably −125 to −75 mmHg.

The embodiments described for the wound care product for use in treatment of wounds comprising microbial biofilm infections also apply to the above method of treatment.

The wound care product may be applied for a period of 10-40 min, such as 15-35 min, preferably 20-30 min. The starting point of these periods is when the wound care product is put in contact with the wound, and the end point is defined as when the negative pressure is applied. The negative pressure may be applied for a period in the range of 0.5-18 h, such as 1-12 h, such as 2-8 h, such as 3-6 h, such as 4 h. Typically the period of applying negative pressure is interrupted by a new application of a fresh wound care product comprising sodium diacetate, whereafter said negative pressure is reapplied as described below. During any given interruption of the negative pressure the wound care product may be exchanged for a fresh one.

In yet another useful embodiment a method is provided, wherein steps a) to d) as described above are repeated, i.e. steps a) to d) are performed followed be performing steps a) to d) again, and so on. This repetitive cycle may be performed any number of times, and advantageously at least until any infection in the wound has been eradicated. The cycle may also be repeated until the wound has healed entirely thereby hindering any reinfection or so called superinfections.

Alternatively, the method may be repeated without involving an exchange of the wound care product but instead a soaking step is used, where the wound care product may be refreshed with additional sodium diacetate and/or other substances in liquid form at a reduced negative pressure (i.e. a higher pressure which is still below ambient pressure). In this embodiment the method comprises the steps of:
i) applying a wound care product as described above to a wound,
ii) applying negative pressure to the wound for 0.5-18 hours,
iii) adjusting the negative pressure to a less negative pressure,
iv) optionally adding additional sodium diacetate to the wound care device
v) optionally repeating steps ii)-iv)

The less negative pressure of step iii) may in the range of −50 mmHg to −5 mmHg, such as −40 mmHg to −15 mmHg, preferably −30 to −20 mmHg, most preferably about −25 mmHg.

Another useful embodiment of the present invention is a method of reducing bacterial growth in bandages by applying sodium diacetate to the bandage. The sodium diacetate may preferably be in dry form. The bacteria may be biofilm bacteria. Bandages may include highly absorbent bandages such as e.g. Drymax® bandages.

Kit Comprising a Wound Care Product

Another aspect of the present invention is a kit comprising a wound care product as described above and an adhesive membrane.

As above, the wound care product may generally comprise a carrier device such as a dressing. A dressing as defined herein is a material that can be applied to a wound, said material being capable of absorbing and releasing a liquid. The dressing material may be nylon, polyester, acrylic, rayon, viscose, cotton (gauze), polyurethane, other polymeric materials, cellulose materials, a reticulate foam or mixtures thereof. In the present context "Reticulate foam" means foam comprising a cross-linked polymer material. Such materials may include but are not limited to: polyurethane-ether, polyacrylate, cellulose, polypropylene fibres, alginate, viscose, agar, or mixtures thereof.

An "adhesive membrane" as defined herein is any membrane capable of covering the dressing provided in the kit while being able to adhere to the surface area surrounding the wound and dressing. It may also adhere to the dressing itself. An example of this would be a self-adhesive plaster, bandage, or tape of sufficient size and shape. A membrane such as a plaster, bandage or tape may advantageously be adapted to allow e.g. tubing to pass through it, e.g. via a cut-through and a central penetrating cut-out. This allows for liquids to be delivered or removed from the dressing and wound area. However, within the meaning of adhesive membrane is also gauze, which does not necessarily comprise an adhesive material, but adheres to the area of the wound via the force, provided by wrapping the gauze around the body-part inflicted with a wound. This may be especially relevant for wounds affecting the limbs, i.e. arms, hands, legs and feet, where gauze may be easier to apply than a plaster or tape, and also may hold the dressing in the desired position better than a plaster or tape.

In yet another embodiment a kit is provided, wherein said kit further comprises a drainage tube. A "drainage tube" as defined herein is a conduit, channel, tube or pipe as defined above capable of transporting liquids away from the dressing and thereby the wound area. The kit may also comprise a pad as described above, which is attachable to the drainage tube. The pad gives the above-mentioned advantages of holding the tube in position and providing a larger area of attachment and suction (if suction is applied).

The kit may in a useful embodiment be adapted for use in combination with NPWT methods, e.g. the drainage tube may be adapted to fit into a NPWT device or pump. The drainage tube may for example be a soft tube, which fits into a pump, for example a peristaltic pump, used for providing a negative pressure. Alternatively the dressing material is selected from materials allowing for a negative pressure to be evenly distributed throughout the wound area. Such a kit is further described in WO2011/076216 FIGS. 13 and 15 which is included herein by reference.

In the context of the present invention "negative pressure" is defined as a pressure within a given volume which is lower than the surrounding pressure, e.g. the ambient pressure which will often be atmospheric pressure. In the present context said volume may be the volume defined by an adhesive membrane, such as a bandage or gauze, placed over an area comprising a wound, preferably comprising a dressing in the wound cavity. The size of the wound, the adhesive membrane and the dressing determines the size of the volume. The volume may also be affected by the compressibility of the dressing. An effect of the negative pressure is to provide for the continuous removal of excess liquids such as exudates from a wound.

It should be noted that embodiments and features described in the context of one of the aspects of the present invention also apply to the other aspects of the invention. All patent and non-patent references cited in the present application, are hereby incorporated by reference in their entirety.

The invention will now be described in further details in the following non-limiting examples.

EXAMPLES

Materials and Methods

Bacterial Strains

The wild-type *P. aeruginosa* PAO1 used for the planktonic and biofilm experiments was obtained from the *Pseudomonas* Genetic Stock Center (www.pseudomonas.med.ecu.edu, strain PAO0001). The wild-type *S. aureus* 8325-4, used for planktonic and biofilm experiments was described by Novick, R. P. 1967. The following bacteria were obtained from the Department of Clinical Microbiology, Copenhagen University Hospital, Denmark: *E. coli* (wild type and clinical ESBL producing strains), *S. aureus* (wild type and clinical MRSA strains) and *Klebsiella pneumoniae* (clinical ESBL producing strain).

Growth Media

For plating, Luria broth (LB) medium mix with 2.0% agar was used. For all experiments including bacterial biofilms, AB minimal medium supplemented with glucose was used except if different is mentioned. AB minimal medium consists of: A standard buffer system consisting of $(NH_4)_2SO_4$ (15.1 mM), $Na_2HPO_4 \cdot 2H_2O$ (33.7 mM) and $KH_2PO_4$ (22.0 mM. NaCl (0.051 M), $MgCl_2$ (1 mM), $CaCl_2$ (0.1 mM), and trace metals (100 µl/liter). The trace metal solution contained $CaSa_4 \cdot 2H_2O$ (200 mg/liter), $FeSO_4 \cdot 7H_2O$ (200 mg/liter), $MnSO_4 \cdot H_2O$ (20 mg/liter), $CuSO_4 \cdot 5H_2O$ (20 mg/liter), $ZnSO_4 \cdot 7H_2O$ (20 mg/liter), $CoSO_4 \cdot 7H_2O$ (10 mg/liter), $NaMoO_4 \cdot H_2O$, and $H_3BO_3$ (5 mg/liter).

Growth of Bacteria

Two types of biofilm setups were used, micropore filter assay and a microtitter plate assay:

The microtitter plate assay is based on biofilms growing in microtiter dishes with AB minimal medium containing 0.3 mM glucose as described by O' toole et al (1999).

The Micro-pore assay is based on biofilms growing on a micropore filter on AB minimal agar plates. The micropore filters are placed on top of an AB minimal agar plate. Bacteria are propagated on the micro-pore filters as spots of 20 µl bacterial suspension and incubated at 37° C. For a biofilm to develop the filters were transferred to a fresh AB minimal agar plate once after 24 hours. The biofilm were mature and ready for use after 48 hours incubation in total, at 37° C. Planktonic cultures were grown in shake flasks at 37° C. The microtitter plate assay for biofilm tolerance to sodium diacetate was assessed by exchanging the AB minimal medium of 24 h old biofilms with AB minimal medium supplemented with different concentrations of sodium diacetate.

Example 1 pH Dependence of Sodium Acetate Concentration

To measure the correlation between dissolved $NaHAc_2$ and pH, increasing amounts (w/v) were added to AB minimal media. The measurements show a decrease in pH with increasing amounts of $NaHAc_2$, as depicted in table 1.

TABLE 1

| % NaHAc2 (w/v) | Media pH |
|---|---|
| 0.00% | 6.82 |
| 0.50% | 5.78 |
| 0.75% | 5.31 |
| 1.00% | 5.09 |
| 1.25% | 4.99 |
| 1.50% | 4.91 |
| 1.75% | 4.86 |
| 2.00% | 4.83 |
| 2.25% | 4.80 |
| 2.50% | 4.78 |
| 2.75% | 4.76 |
| 3.00% | 4.74 |

Example 2

Concentration Dependence of Sodium Diacetate Kill Rate

To elucidate the concentration dependency of the antimicrobial effect of $NaHAc_2$ static 24 hour old biofilms grown in microtitter plates were treated for another 24 hours with increasing amounts of $NaHAc_2$ as depicted in table 2 with the decrease in pH as seen from table 1. The antimicrobial effect was determined by plating the treated and non-treated biofilm. To ensure complete removal of all adhering bacteria the wells of the microtitter plate were washed mechanically. We observed a complete killing effect of the biofilm using 1.75% (w/v) added $NaHAc_2$ and higher. Surprisingly, we did not observe the strict pH dependent killing for $NaHAc_2$ which we previously had observed using acetic acid. We even observed partial killing, with even the lowest concentrations of $NaHAc_2$.

TABLE 2

| % NaHAc2 (w/v) | Average CFU |
|---|---|
| 3% | 0 |
| 2.75% | 0 |
| 2.50% | 0 |
| 2.25% | 0 |
| 2.00% | 0 |
| 1.75% | 0 |
| 1.50% | 1.98E+03 |
| 1.25% | 1.96E+05 |
| 1.00% | 8.05E+06 |
| 0.75% | 9.63E+07 |
| 0.50% | 3.12E+08 |
| 0.25% | 1.15E+09 |
| 0% | 5.69E+09 |

Example 3

Effect of Dry Sodium Diacetate on Microbial Biofilm

To elucidate the efficacy of dry sodium diacetate on microbial biofilms of *P. aeruginosa*. Bacteria were propagated on a micropore filter for biofilm formation. The Micro-pore filters were placed on top of an LB-agar plate. Bacteria were spread on the micro-pore filters as spots and incubated at 37° C. For a biofilm to develop the filters were transferred to a fresh LB-agar plate once after 24 hours. The biofilm were mature and ready for use after 48 hours incubation in total, at 37° C.

After 48 hours NaHAc$_2$ was added on top of the biofilm spot, either directly or between two pieces of gauze. The control was plain gauze. All treatments were incubated for 24 hours. The effect was evaluated by replication of the micro pore filter after treatment. The endpoint was growth or no growth of bacteria after the treatment. As seen from FIG. 3 the presence of NaHAc$_2$ completely eradicates the bacteria. This is in striking contrast to the control which is not affected by the gauze (data not shown).

Figure 1:
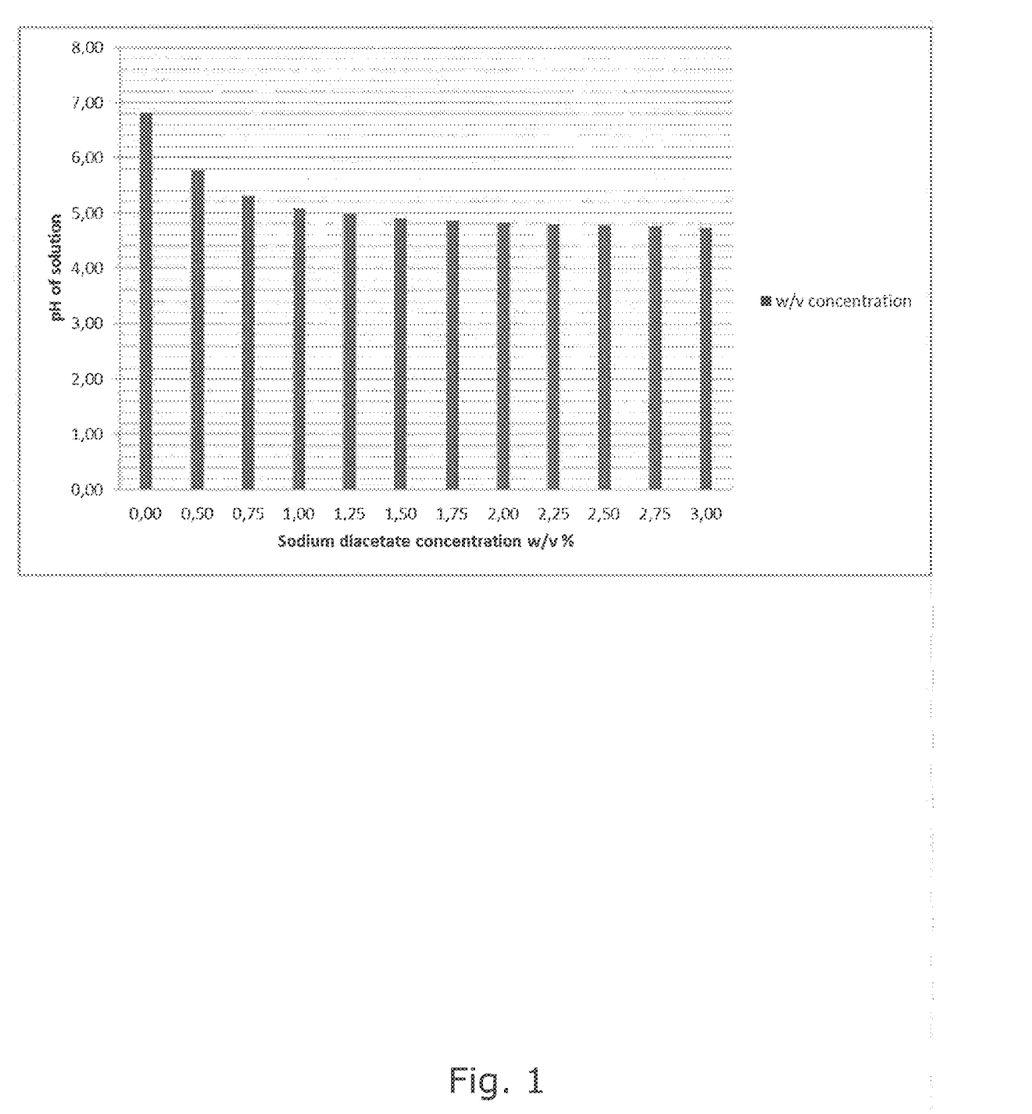
FIG. 1 shows the pH of an aqueous AB minimal media as a function of the percentage (weight/volume) of sodium diacetate (NaHAc$_2$) added to the medium. The graph shows how the pH of the medium decreases from the initial value of pH 6.82 at zero added sodium diacetate, down to a value of approximately pH 4.75 at 3 g/L of sodium diacetate. It is clear that the pH value levels out already at around 1.5 g/L sodium diacetate, and only becomes marginally more acidic up to 3 g/L, demonstrating a build in buffer effect of the sodium diacetate salt.
Figure 2:
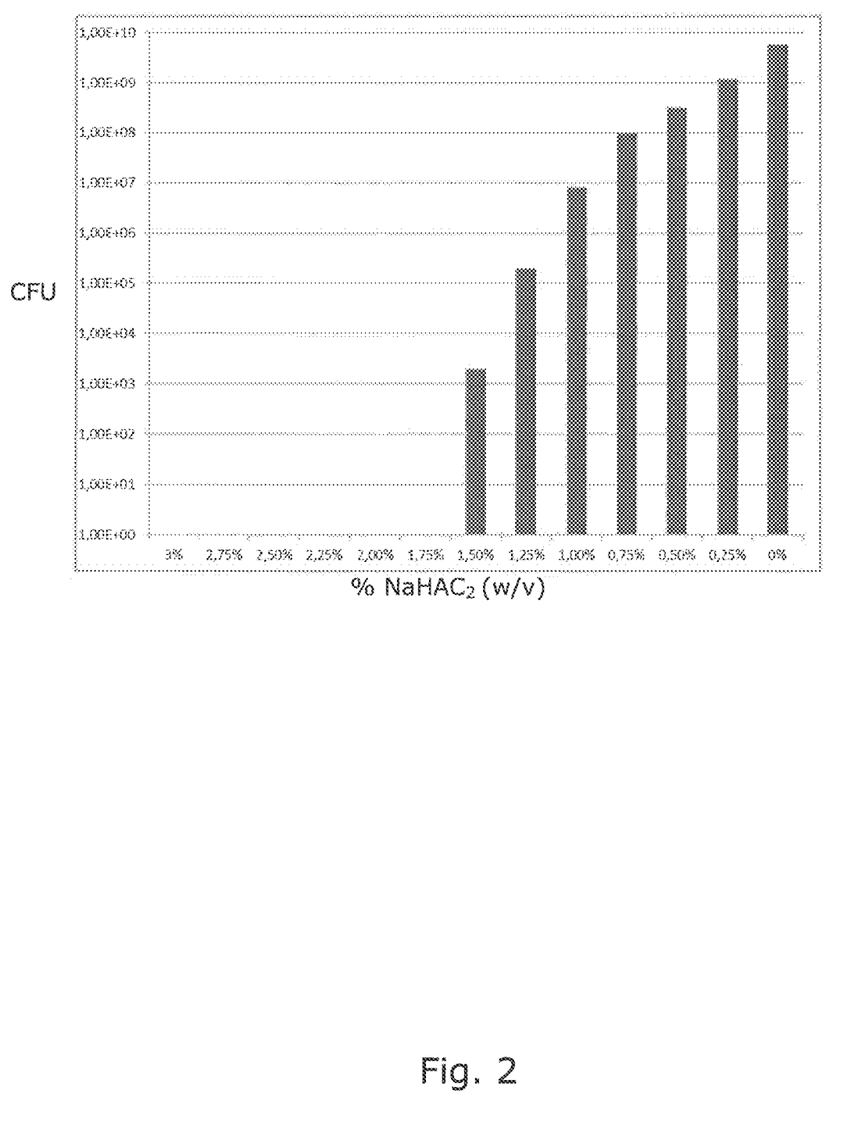
FIG. 2 shows the antimicrobial effect of increasing concentrations of sodium diacetate (NaHAc2) in aqueous compositions on 24 hours old static P, aeruginosa biofilms grown in AB minimal medium. The graph shows an effect of the salt already at 0.25% (W/V), and complete killing of the biofilm bacteria at 1.75% (W/V), the latter corresponding to an acidity of pH 4.86. The biofilm bacteria were harvested and plated on LB plates in order to determine the CFU after treatment.
Figure 3:
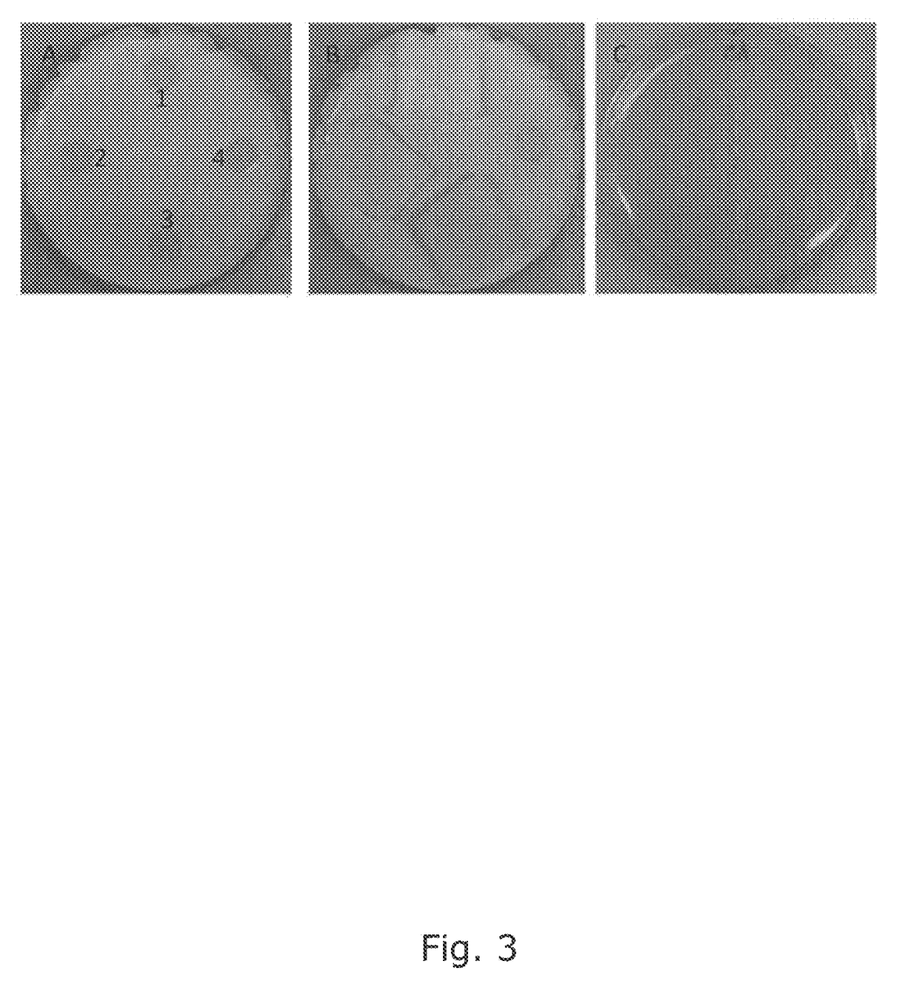
FIG. 3 shows the effect of adding sodium diacetate powder to a mature biofilm (*P. aeruginosa*), grown on a micropore filter. Frame A shows the untreated bacterial biofilm spots, frame B the treatment and frame C, the complete eradication of bacteria caused by the treatment in terms of no growth by replication of the micro pore filter after treatment. The treatments were as follows: 1) sodium diacetate dry between gauze, 2) sodium diacetate between gauze soaked in wounds buffer, 3) sodium diacetate foam soaked in wounds buffer and 4) sodium diacetate dry.

FIG. 3, frame A shows the untreated bacterial biofilm spots, frame B the treatment and frame C, the complete eradication of bacteria caused by the treatment. The treatments were as follows: 1) sodium diacetate dry between gauze, 2) sodium diacetate between gauze soaked in wounds buffer, 3) sodium diacetate foam soaked in wounds buffer and 4) sodium diacetate dry.

Example 4

Effect of Dry Sodium Diacetate on Further Microbial Biofilm

Figure 4:
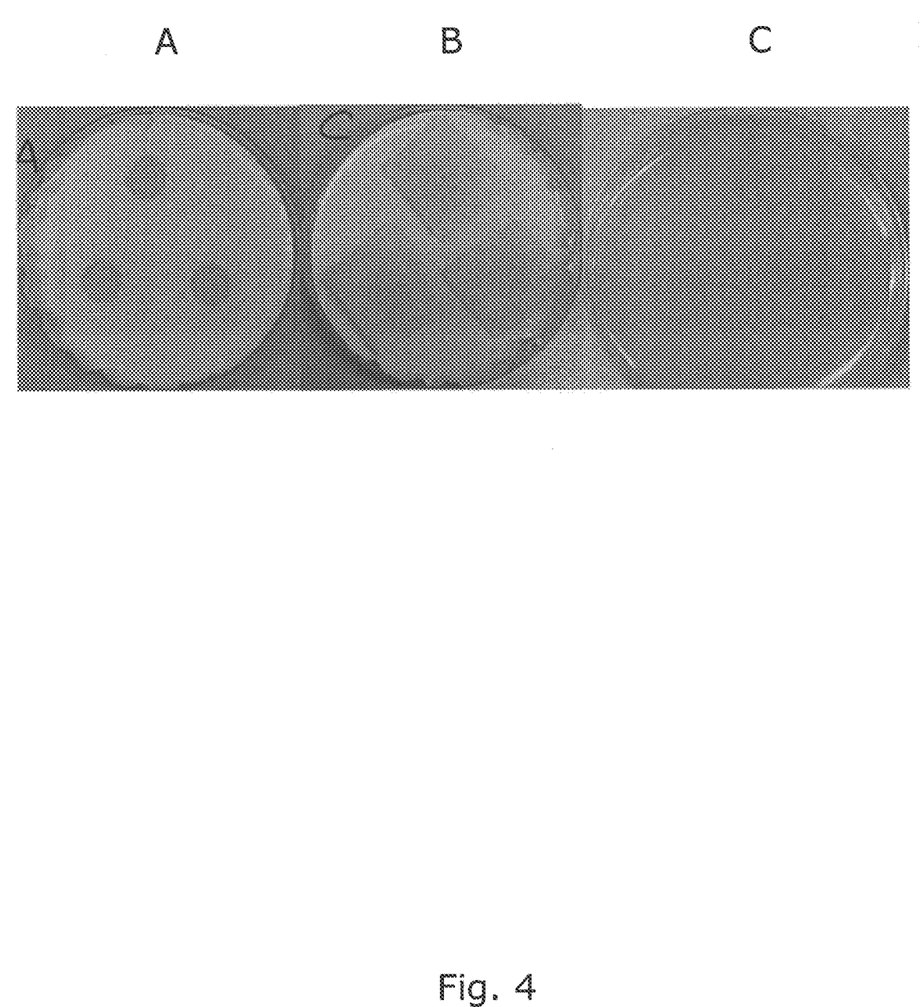
FIG. 4 shows the effect of adding sodium diacetate powder to a mature biofilm (*E. Coli*), grown on a micropore filter. Frame A shows the untreated bacterial biofilm spots, frame B the treatment and frame C, the complete eradication of bacteria caused by the treatment in terms of no growth by replication of the micro pore filter after treatment. The treatments were as follows: sodium diacetate dry between gauze, sodium diacetate between gauze soaked in wounds buffer, and sodium diacetate foam soaked in wounds buffer.

The in vitro effect of dry sodium diacetate presented in example 3 was confirmed for biofilms by the same method as in example 3 for:
*E. coli* (wild type and clinical ESBL producing strains) (See FIG. 4)
*S. aureus* (wild type and clinical MRSA strains) and *Klebsiella pneumoniae* (clinical ESBL producing strain).

For all these bacteria, the biofilm infection was completely eradicated by treatment with sodium diacetate.

Example 5

Wound Treatment and Clinical Trials

To elucidate the clinical potential of sodium diacetate in wound care human clinical trials are being performed in a hospital setting to test the efficacy of dressings incorporating sodium diacetate on bacterially infected chronic wounds.

Dressings are used employing 0.2 mg/cm$^2$ or less of sodium diacetate on the surface of the dressing material. Incorporating smaller amounts of sodium diacetate is tested incrementally. Initial trials are performed using negative pressure wound therapy in combination with dressings incorporating sodium diacetate as described herein. Trials are performed on test subjects having chronic wounds due to infection with for example *P. aeruginosa* and with reduced immune responses due to for example, drug abuse, diabetes, or obesity.

Initial results indicate that the infections are eradicated and wound healing is accelerated on the basis hereof.

REFERENCES

WO 2009/155931
Martineau, L. et al., Journal of Applied Microbiology (2007), 103, 297-304
WO2005/123057
US 2010/0068279
WO2011/076216
Høiby, N et al., Int J Antimicrob Agents, 2010, 35(4), page 322

The invention claimed is:

1. A wound care product configured to treat wound infections comprising microbial biofilm, the wound care product consisting of an amount of sodium diacetate in dry form, the amount effective for treating a microbial biofilm infection within a wound area, and a carrier device including the amount of sodium diacetate embedded within a portion thereof and configured to place the amount of sodium diacetate into direct contact with the wound, wherein the sodium diacetate is the only active ingredient provided in the wound care product.

2. The wound care product according to claim 1, wherein the sodium diacetate is a powder.

3. The wound care product according to claim 1, wherein the particle size of sodium diacetate is in the range of 2 mm to 0.001 mm.

4. The wound care product according to claim 1, wherein sodium diacetate is embedded in the carrier device in an amount in the range of 0.01-200 mg/cm3.

5. The wound care product according to claim 1, wherein sodium diacetate is distributed on a surface of the carrier device in an amount in the range of 0.01-2 mg/cm2.

6. The wound care product according to claim 1, wherein the carrier device is selected from a group consisting of a dressing, foam, gauze, bandage, gel, or paste.

7. The wound care product according to claim 1, wherein sodium diacetate is the only antimicrobial and/or antibacterial ingredient in said product.

8. A kit comprising the wound care product according to claim 1 and an adhesive membrane.

* * * * *